(12) United States Patent
Chen et al.

(10) Patent No.: US 9,416,093 B2
(45) Date of Patent: Aug. 16, 2016

(54) SUPPORTED QUATERNARY PHOSPHONIUM CATALYST, PREPARATION AND USE THEREOF

(71) Applicants: CHINA PETROLEUM & CHEMICAL CORPORATION, Beijing (CN); SHANGHAI RESEARCH INSTITUTE OF PETROCHEMICAL TECHNOLOGY, SINOPEC, Shanghai (CN)

(72) Inventors: Liangfeng Chen, Shanghai (CN); Wenjun He, Shanghai (CN)

(73) Assignees: China Petroleum & Chemical Corporation, Beijing (CN); Shanghai Research Institute of Petrochemical Technology, Sinopec, Shanghai (CN)

(*) Notice: Subject to any disclaimer, the term of this patent is extended or adjusted under 35 U.S.C. 154(b) by 32 days.

(21) Appl. No.: 13/894,803

(22) Filed: May 15, 2013

(65) Prior Publication Data

US 2013/0317179 A1      Nov. 28, 2013

(30) Foreign Application Priority Data

May 16, 2012 (CN) .......................... 2012 1 0150361
May 16, 2012 (CN) .......................... 2012 1 0150443

(51) Int. Cl.
   *C07C 68/06* (2006.01)
   *C07F 9/54* (2006.01)
   *C07D 317/38* (2006.01)

(52) U.S. Cl.
   CPC ............ *C07C 68/065* (2013.01); *C07D 317/38* (2013.01); *C07F 9/5407* (2013.01); *C07F 9/5449* (2013.01)

(58) Field of Classification Search
   None
   See application file for complete search history.

(56) References Cited

U.S. PATENT DOCUMENTS

| 6,207,850 | B1 | 3/2001 | Jiang et al. | |
| 6,407,279 | B1* | 6/2002 | Buchanan et al. | 558/277 |
| 2005/0080287 | A1 | 4/2005 | Buchanan et al. | |
| 2008/0214386 | A1* | 9/2008 | Takahashi et al. | 502/162 |
| 2011/0040117 | A1 | 2/2011 | Risse et al. | |

FOREIGN PATENT DOCUMENTS

| CN | 101121147 A | 2/2008 |
| CN | 101249452 A | 8/2008 |
| CN | 102126957 A | 7/2011 |
| WO | WO 00/73256 A1 | 12/2000 |
| WO | WO 01/56971 A | 8/2001 |
| WO | WO 2010/063780 A1 | 6/2010 |

OTHER PUBLICATIONS

Takahashi, Chem. Commun., 2006, 1664-1666.*
Tundo, J. Am. Chem. Soc., vol. 101, No. 22, 1979, p. 6606-6613.*
Tundo, J. Am. Chem. Soc., vol. 104, No. 24, 1982, p. 6551-6555.*
Nishikubo, Journal of Polymer Science Part A: Polymer Chemistry, vol. 31, Issue 4, pp. 939-947, Mar. 30, 1993.*
Bhanage, B.M. et al., Concurrent Synthesis of Dimethyl Carbonate and Ethylene Glycol via Transesterification of Ethylene Carbonate and Methanol using Smectite Catalysts Containing Mg and/or Ni, Catal. Lett. 83, Nos. 3-4 (2002), pp. 137-141.
Kawabe, K., "Development of Highly Selective Process for Mono-Ethylene Glycol Production from Ethylene Oxide via Ethylene Carbonate Using Phosphonium Salt Catalyst," Catal. Surv. Asia 14 (2010), pp. 111-115.
Knifton, J.F. et al, "Ethylene Glycol-Dimethyl Carbonate Cogeneration," J. Mol. Catal. A 67 (1991), pp. 389-399.
Cao, M. et al., "Synthesis of Dimethyl Carbonate (DMC) From $CO_2$, Ethylene Oxide and Methanol Using Heterogeneous Anion Exchange Resins as Catalysts," React. Kinet. Catal. Lett. 88 (2006), pp. 251-259.
Bhange, B.M. et al., "Synthesis of Dimethyl Carbonate and Glycols from Carbon Dioxide, Epoxides, and Methanol Using Heterogeneous Basic Metal Oxide Catalysts with High Activity and Selectivity," Appl. Catal. A 219 (2001), pp. 259-266.
Zhu et al., "Synthesis of Propylene Glycol and Dimethyl Carbonate Using Polymer-Supported Catalysts," *Chinese Chemical Letters*, 7(6): 519-522 (1996), 4 pages.

* cited by examiner

*Primary Examiner* — Robert C Boyle
(74) *Attorney, Agent, or Firm* — Finnegan, Henderson, Farabow, Garrett & Dunner, LLP

(57) ABSTRACT

This invention relates to a supported quaternary phosphonium catalyst, preparation thereof and use thereof in producing dialkyl carbonates. The supported quaternary phosphonium catalyst of this invention has the following average molecular structure (I), and is characterized by a relatively high and stable catalyst activity.

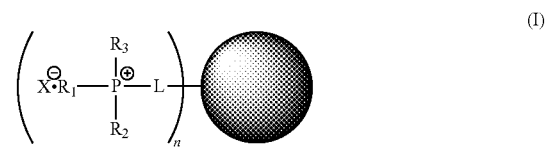

wherein, each of X, L, n, $R_1$, $R_2$, $R_3$ and

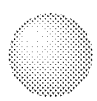

is the same as that in the specification.

22 Claims, No Drawings

SUPPORTED QUATERNARY PHOSPHONIUM CATALYST, PREPARATION AND USE THEREOF

TECHNICAL FIELD

This invention relates to a quaternary phosphonium catalyst, specifically to a supported quaternary phosphonium catalyst. This invention further relates to a process for producing the supported quaternary phosphonium catalyst and use thereof in producing dialkyl carbonates.

BACKGROUND ART

Dialkyl carbonates (especially dimethyl carbonate) have found extensive use in the chemistry industry. With relatively gentle reaction conditions, high yield and co-production of glycols, the transesterification process has been valued as the most promising process in industry for producing dialkyl carbonates.

Generally, the transesterification reaction takes an alkali metal hydroxide, an alkali metal carbonate or an alkali metal alkoxylate as the catalyst, which are of homogeneous type and therefore are difficult to separate from the reaction products. A catalyst produced by supporting an alkali metal or alkali metal salt onto a carrier is vulnerable to water or $CO_2$ in the air, which may decrease the catalyst activity significantly. Metal oxide type catalysts, alkali (earth) metal exchanged zeolite type catalysts or clay type catalysts suffer from a relatively low activity or selectivity. Ion exchange resin type catalysts like quaternary amine or tertiary amine based catalysts suffer from unstable catalyst activity since N elements contained therein is easily detachable after long-term use.

Therefore, there is still a need in the prior art for a catalyst for producing dialkyl carbonates, which can be produced by a simple and industrially favorable process, and with which, the aforesaid drawbacks in connection with the prior art catalysts can be effectively overcome.

INVENTION SUMMARY

The present inventors conducted an extensive study on the prior art, and finally found a specific supported quaternary phosphonium catalyst, which is characterized by a relatively high and stable catalyst activity, and when used as the catalyst in producing dialkyl carbonates by a transesterification process, the aforesaid drawbacks in connection with the prior art catalysts can be effectively overcome, whereby achieving this invention.

Specifically, this invention relates to the following aspects:

1. A supported quaternary phosphonium catalyst, having the following average molecular structure (I):

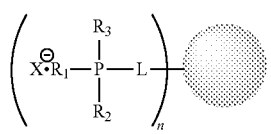
(I)

wherein X is a halogen atom (preferably Cl, Br or I, more preferably Br or I), $R_1$, $R_2$ and $R_3$ are different from or identical to each other, and are each independently selected from the group consisting of an optionally substituted $C_{1-20}$ straight-chain or branched alkyl, an optionally substituted $C_{2-20}$ straight-chain or branched alkenyl, an optionally substituted $C_{2-20}$ straight-chain or branched alkynyl, an optionally substituted $C_{3-20}$ cycloalkyl or an optionally substituted $C_{6-20}$ aryl (preferably a $C_{2-10}$ straight-chain or branched alkyl, a $C_{2-10}$ straight-chain or branched alkyl substituted by one or more phenyl or $C_{3-20}$ cycloalkyl, a $C_{2-10}$ straight-chain or branched alkenyl, a $C_{2-10}$ straight-chain or branched alkenyl substituted by one or more phenyl or $C_{3-20}$ cycloalkyl, a $C_{3-20}$ cycloalkyl, a $C_{3-20}$ cycloalkyl substituted by one or more $C_{1-6}$ straight-chain or branched alkyl or $C_{2-6}$ straight-chain or branched alkenyl, a $C_{6-20}$ aryl, or a $C_{6-20}$ aryl substituted by one or more $C_{1-6}$ straight-chain or branched alkyl or $C_{2-6}$ straight-chain or branched alkenyl), L is a bivalent bonding group (preferably selected from the group consisting of an optionally substituted $C_{1-20}$ straight-chain or branched alkylene, an optionally substituted $C_{2-20}$ straight-chain or branched alkenylene or an optionally substituted $C_{2-20}$ straight-chain or branched alkynylene, more preferably selected from the group consisting of a $C_{1-20}$ straight-chain or branched alkylene, more preferably selected from the group consisting of a $C_{2-8}$ straight-chain alkylene, wherein the alkylene, the alkenylene or the alkynylene is optionally interfered by one or more (for example one to three, one to two, or one) interfering group selected from the group consisting of —O—, —S—, —$NR_a$— ($R_a$ is a $C_{1-4}$ alkyl) and phenylene (preferably phenylene)),

is a carrier (preferably one or more selected from the group consisting of an organic carrier and an inorganic carrier, more preferably one or more selected from the group consisting of an inorganic carrier, more preferably one or more selected from the group consisting of silica, zeolite (preferably SBA-15, MCM-41, MCF, HMS, KIT-6 or SBA-16) and kieselguhr), — represents a covalent bond,
• represents an ionic bond,
n is an averaged number such that the ratio by weight of the moiety

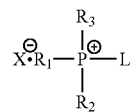

(also referred to as the quaternary phosphonium group) to the moiety

(the carrier) is 1 to 25:75 to 99, preferably 1 to 20:80 to 99.

2. The supported quaternary phosphonium catalyst according to any of the aforesaid aspects, having an elution loss D of less than 2%, preferably less than 1.5%, more preferably less than 1%, more preferably less than 0.8%, further more preferably less than 0.5%, wherein the elution loss D is determined according to a method comprising weighting 2 g of the supported quaternary phosphonium catalyst with a P content of P1 (unit: wt %), (1) suspending the supported quaternary phosphonium catalyst in 40 ml methanol, stirring (at a stirring speed of 100 rpm) the resultant at 100° C. for 4 h, then immediately filtering the resultant so as to separate the supported quaternary phosphonium catalyst, (2) then, suspending the separated supported quaternary phosphonium catalyst in 40 ml methanol, stirring (at a stirring speed of 100 rpm) the resultant at 100° C. for 4 h, then immediately filtering the resultant so as to separate the supported quaternary phosphonium catalyst, repeating the process (2) for further 10 times, and then determining the P content of the finally separated supported quaternary phosphonium catalyst as P2 (unit: wt %), and then calculating the elution loss D as follows:

$$D=(P1-P2)/P1\times 100\%.$$

3. A process for producing a supported quaternary phosphonium catalyst, comprising a step of reacting a tertiary phosphine of the following formula (2) with a macromolecular agent of the following formula (3), wherein the ratio by weight of the tertiary phosphine to the macromolecular agent is 1 to 20:80 to 99, preferably 1 to 15:85 to 99,

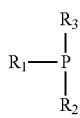

(2)

wherein $R_1$, $R_2$ and $R_3$ are different from or identical to each other, and are each independently selected from the group consisting of an optionally substituted $C_{1-20}$ straight-chain or branched alkyl, an optionally substituted $C_{2-20}$ straight-chain or branched alkenyl, an optionally substituted $C_{2-20}$ straight-chain or branched alkynyl, an optionally substituted $C_{3-20}$ cycloalkyl or an optionally substituted $C_{6-20}$ aryl (preferably a $C_{2-10}$ straight-chain or branched alkyl, a $C_{2-10}$ straight-chain or branched alkyl substituted by one or more phenyl or $C_{3-20}$ cycloalkyl, a $C_{2-10}$ straight-chain or branched alkenyl, a $C_{2-10}$ straight-chain or branched alkenyl substituted by one or more phenyl or $C_{3-20}$ cycloalkyl, a $C_{3-20}$ cycloalkyl, a $C_{3-20}$ cycloalkyl substituted by one or more $C_{1-6}$ straight-chain or branched alkyl or $C_{2-6}$ straight-chain or branched alkenyl, a $C_{6-20}$ aryl, or a $C_{6-20}$ aryl substituted by one or more $C_{1-6}$ straight-chain or branched alkyl or $C_{2-6}$ straight-chain or branched alkenyl),
— represents a covalent bond,

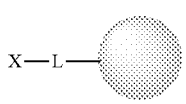

(3)

wherein X is a halogen atom (preferably Cl, Br or I, more preferably Br or I), L is a bivalent bonding group (preferably selected from the group consisting of an optionally substituted $C_{1-20}$ straight-chain or branched alkylene, an optionally substituted $C_{2-20}$ straight-chain or branched alkenylene or an optionally substituted $C_{2-20}$ straight-chain or branched alkynylene, more preferably selected from the group consisting of a $C_{1-20}$ straight-chain or branched alkylene, more preferably selected from the group consisting of a $C_{2-8}$ straight-chain alkylene, wherein the alkylene, the alkenylene or the alkynylene is optionally interfered by one or more (for example one to three, one to two, or one) interfering group selected from the group consisting of —O—, —S—, —$NR_a$— ($R_a$ is a $C_{1-4}$ alkyl) and phenylene (preferably phenylene)),

is a carrier (preferably one or more selected from the group consisting of an organic carrier and an inorganic carrier, more preferably one or more selected from the group consisting of an inorganic carrier, more preferably one or more selected from the group consisting of silica, zeolite (preferably SBA-15, MCM-41, MCF, HMS, KIT-6 or SBA-16) and kieselguhr),
— represents a covalent bond.

4. The process according to any of the aforesaid aspects, wherein the reaction temperature is 100 to 190° C., preferably 120 to 190° C., and the reaction duration is 10 to 40 h, preferably 10 to 30 h.

5. The process according to any of the aforesaid aspects, wherein the carrier is one or more selected from the group consisting of silica, zeolite (preferably SBA-15, MCM-41, MCF, HMS, KIT-6 or SBA-16) and kieselguhr, and the macromolecular agent is produced by a reaction between the carrier and a halogenation agent of the following formula (4), wherein the ratio by weight of the halogenation agent to the carrier is 0.005 to 0.15:1, preferably 0.01 to 0.1:1,

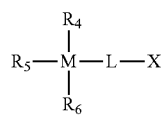

(4)

wherein X is a halogen atom (preferably Cl, Br or I, more preferably Cl), L is a bivalent bonding group (preferably selected from the group consisting of an optionally substituted $C_{1-20}$ straight-chain or branched alkylene, an optionally substituted $C_{2-20}$ straight-chain or branched alkenylene or an optionally substituted $C_{2-20}$ straight-chain or branched alkynylene, more preferably selected from the group consisting of a $C_{1-20}$ straight-chain or branched alkylene, more preferably selected from the group consisting of a $C_{2-8}$ straight-chain alkylene, wherein the alkylene, the alkenylene or the alkynylene is optionally interfered by one or more (for example one to three, one to two, or one) interfering group selected from the group consisting of —O—, —S—, —$NR_a$— ($R_a$ is a $C_{1-4}$ alkyl) and phenylene (preferably phenylene)), M is Ti, Si or Zr, preferably Si, $R_4$, $R_5$ and $R_6$ are different from or identical to each other, and are each independently selected from the group consisting of a $C_{1-4}$ straight-chain or branched alkoxy, preferably methoxy or ethoxy.

6. The process according to any of the aforesaid aspects, wherein the reaction temperature is 70 to 140° C., preferably 90 to 120° C., and the reaction duration is 1 to 60 h, preferably 5 to 48 h.

7. The process according to any of the aforesaid aspects, wherein said X is Cl, and the process further comprises a step of contacting the macromolecular agent with one or more modifying agent selected from the group consisting of a bromination agent (preferably an alkali metal bromide, more preferably one or more selected from the group consisting of LiBr, NaBr, KBr and CsBr) and an iodization agent (preferably an alkali metal iodide, more preferably one or more selected from the group consisting of LiI, NaI, KI and CsI) before reacting the macromolecular agent with the tertiary phosphine, wherein the ratio by weight of the modifying agent to the macromolecular agent is 0.01 to 1:1, preferably 0.02 to 0.6:1.

8. Use of the supported quaternary phosphonium catalyst according to any of the aforesaid aspects or a supported quaternary phosphonium catalyst produced in line with the process according to any of the aforesaid aspects as a catalyst in co-producing a di-$C_{1-10}$alkyl carbonate and a $C_{2-10}$ alkanediol by a transesterification process.

9. A process for producing a dialkyl carbonate, comprising a step of contacting a $C_{2-10}$ alkylene carbonate (preferably ethylene carbonate or propylene carbonate) with a monohydric $C_{1-10}$ alkanol (preferably methanol) in the presence of the supported quaternary phosphonium catalyst according to any of the aforesaid aspects or a supported quaternary phosphonium catalyst produced in line with the process according to any of the aforesaid aspects, to produce a di-$C_{1-10}$alkyl carbonate (preferably dimethyl carbonate) and a $C_{2-10}$ alkanediol (preferably ethylene glycol or propylene glycol).

10. The process according to any of the aforesaid aspects, wherein the reaction temperature is 60 to 140° C., preferably 80 to 140° C., the reaction duration is 0.1 to 20 h, preferably 1 to 10 h, the ratio by mol of the monohydric $C_{1-10}$ alkanol to the $C_{2-10}$ alkylene carbonate is 2 to 10:1, preferably 2 to 6:1, and the ratio by weight of the supported quaternary phosphonium catalyst to the $C_{2-10}$ alkylene carbonate is 0.005 to 0.5:1, preferably 0.01 to 0.2:1.

Technical Effects

The supported quaternary phosphonium catalyst according to this invention shows advantages as follows.

According to this invention, the supported quaternary phosphonium catalyst is physically/chemically stable, and therefore will not degrade even after long-term storage, which facilitates its further use.

According to this invention, the supported quaternary phosphonium catalyst is stable and steady in catalyst activity, less vulnerable to degradation by the reaction conditions or ambient environments, and even after long-term use or multiple times of recycling, the activity thereof will retain to a significant extent (decreased by less than 5%, preferably by less than 2%).

According to this invention, in the supported quaternary phosphonium catalyst, the catalyst active group (the quaternary phosphonium group) bonds with the carrier by a strong chemical bond (the covalent bond), whereby establishing a firm and strong bonding therebetween, and even after long-term use or multiple times of recycling, the catalyst active group will not be detached to a significant extent.

According to this invention, the supported quaternary phosphonium catalyst can be easily regenerated if the catalyst activity decreases to an unacceptable level, and therefore is characterized by low cost both in production and in use.

According to this invention, by controlling the load/density of the group X-L- on the macromolecular agent and/or by controlling the ratio of the tertiary phosphine to the macromolecular agent to be used, it is easy to control the load/density of the quaternary phosphonium group on the carrier, whereby freely controlling the catalyst activity of the supported quaternary phosphonium catalyst.

According to this invention, the catalyst activity and selectivity of the supported quaternary phosphonium catalyst is so high that when used as the catalyst in producing dialkyl carbonates by a transesterification process, it is possible to co-produce dialkyl carbonates and glycols with a high yield.

According to one embodiment of this invention, when the supported quaternary phosphonium catalyst was used as the catalyst in producing dimethyl carbonate by the transesterification reaction of ethylene carbonate with methanol, under the conditions of a reaction temperature of 100° C., the ratio by mol of methanol to ethylene carbonate of 4:1, the ratio by weight of the catalyst to ethylene carbonate of 0.05:1, a reaction duration of 4 h, the ethylene carbonate conversion was as high as 49.2%, the selectivity to dimethyl carbonate was as high as 98.9%, the selectivity to ethylene glycol was as high as 98.7%, and after recycled for 5 times, the catalyst activity decreased by less than 2%.

BEST MODE TO CARRY OUT THIS INVENTION

This invention will be described in details hereinafter h reference to the following specific embodiments. However, it is known that the protection scope of this invention should not be construed as limited to these specific embodiments, but rather determined by the attached claims.

In the context of this specification, if a material, process/step, part, apparatus or device is described as "known to a person skilled in the art" or "normally known in this field" or the like, it refers to that has been normally used in this field by the date at which this application is filed, and further to that has not been widely used in this field by this date, but will be for a similar purpose.

In the context of this specification, the term "halogen atom" refers to F, Cl, Br and I.

In the context of this specification, the expression "optionally substituted" refers to optionally substituted by one or more (for example 1-5, 1-4, 1-3, 1-2 or 1) substituent selected from the group consisting of a halogen atom, a $C_{1-6}$ straight-chain or branched alkyl, a $C_{1-6}$ straight-chain or branched haloalkyl, a $C_{2-6}$ straight-chain or branched alkenyl, a $C_{2-6}$ straight-chain or branched akynyl, a $C_{1-6}$ straight-chain or branched alkoxy, a $C_{3-20}$ cycloalkyl, a $C_{3-20}$ cycloalkyl $C_{1-6}$ straight-chain or branched alkyl, a $C_{3-20}$ cycloalkyl $C_{1-6}$ straight-chain or branched alkoxy, a $C_{6-20}$ aryl, a $C_{6-20}$ aryl $C_{1-6}$ straight-chain or branched alkyl and a $C_{6-20}$ aryl $C_{1-6}$ straight-chain or branched alkoxy. As the substituent, the halogen atom, the $C_{1-6}$ straight-chain or branched alkyl, the $C_{3-20}$ cycloalkyl, the $C_{3-20}$ cycloalkyl $C_{1-6}$ straight-chain or branched alkyl, the $C_{6-20}$ aryl or the $C_{6-20}$ aryl $C_{1-6}$ straight-chain or branched alkyl is more preferred, the $C_{3-20}$ cycloalkyl or the $C_{6-20}$ aryl is more preferred.

In the context of this specification, the term "$C_{3-20}$ cycloalkyl" refers to a monocyclic, bicyclic or polycyclic alkyl having a ring carbon atom number of 3 to 20. For example a monocyclic alkyl like cyclohexyl, cyclopropyl and cyclopentyl, and a spiro, bridged, or fused bicyclic or polycyclic alkyl like biscyclopentyl, decalinyl, adamantanyi, spiro[2.4]heptyl, spiro[4.5]decyl, bicyclo[3.2.1]octanyl, tricyclo[2.2.1.0$^{2,6}$]octanyl or norbornanyl, can be exemplified. As the $C_{3-20}$ cycloalkyl, the monocyclic $C_{6-10}$ alkyl is more preferred. In the context of this specification, the term "$C_{6-20}$ aryl" refers to an aromatic hydrocarbyl having a ring carbon atom number of 6 to 20. For example, phenyl, a group obtained by directly linking two or more (for example 2-6, 2-5, 2-4 or 2-3) benzene rings by a single bond, for example biphenyl and triphenyl, and a group obtained by fusing two or more (for example 2-6, 2-5, 2-4 or 2-3) benzene rings, for example naphthyl, anthryl or phenanthryl, can be exemplified. As the $C_{6-20}$ aryl, phenyl, biphenyl and naphthyl are more preferred, phenyl is more preferred.

In the context of this specification, the term "conversion" refers to the single-pass conversion, i.e. the conversion observed after a single contact of the reactant (for example ethylene carbonate) with the catalyst. Similarly, in the context of this specification, the term "selectivity" refers to the single-pass selectivity.

Finally, any percentage, ratio, part or the like mentioned in the context of this specification intends to be calculated on a weight base, unless otherwise expressively specified or a weight base seems unreasonable to a person skilled in the art.

Specifically, this invention relates to a supported quaternary phosphonium catalyst having the following average molecular structure (I):

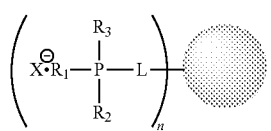
(I)

wherein X is a halogen atom, $R_1$, $R_2$ and $R_3$ are different from or identical to each other, and are each independently selected from the group consisting of an optionally substituted $C_{1-20}$ straight-chain or branched alkyl, an optionally substituted $C_{2-20}$ straight-chain or branched alkenyl, an optionally substituted $C_{2-20}$ straight-chain or branched alkynyl, an optionally substituted $C_{3-20}$ cycloalkyl or an optionally substituted $C_{6-20}$ aryl, L is a bivalent bonding group,

is a carrier, —— represents a covalent bond, • represents an ionic bond, n is an averaged number such that the ratio by weight of the moiety

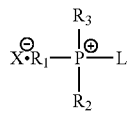

(also referred to as the quaternary phosphonium group) to the moiety

(the carrier) is 1 to 25:75 to 99.

According to this invention, the X preferably represents Cl, Br or I, more preferably represents Br or I.

According to this invention, preferably the $R_1$, $R_2$ and $R_3$ are different from or identical to each other, are each independently selected from the group consisting of a $C_{2-10}$ straight-chain or branched alkyl, a $C_{2-10}$ straight-chain or branched alkyl substituted by one or more (for example 1-4, 1-3, 1-2 or 1) phenyl or $C_{3-20}$ cycloalkyl, a $C_{2-10}$ straight-chain or branched alkenyl (for example allyl), a $C_{2-10}$ straight-chain or branched alkenyl substituted by one or more (for example 1-4, 1-3, 1-2 or 1) phenyl or $C_{3-20}$ cycloalkyl, a $C_{3-20}$ cycloalkyl, a $C_{3-20}$ cycloalkyl substituted by one or more (for example 1-4, 1-3, 1-2 or 1) $C_{1-6}$ straight-chain or branched alkyl or $C_{2-6}$ straight-chain or branched alkenyl, a $C_{6-20}$ aryl (for example phenyl) or a $C_{6-20}$ aryl substituted by one or more (for example 1-4, 1-3, 1-2 or 1) $C_{1-6}$ straight-chain or branched alkyl or $C_{2-6}$ straight-chain or branched alkenyl.

According to this invention, the L is preferably selected from the group consisting of an optionally substituted $C_{1-20}$ straight-chain or branched alkylene, an optionally substituted $C_{2-20}$ straight-chain or branched alkenylene or an optionally substituted $C_{2-20}$ straight-chain or branched alkynylene.

According to this invention, the L is more preferably selected from the group consisting of a $C_{1-20}$ straight-chain or branched alkylene, more preferably a $C_{2-8}$ straight-chain alkylene.

According to this invention, the alkylene, alkenylene or alkynylene in said L may be optionally interfered by one or more (for example one to three, one to two, or one) interfering group selected from the group consisting of —O—, —S—, —$NR_a$— ($R_a$ is a $C_{1-4}$ alkyl) and phenylene at any appropriate position. As the interfering group, phenylene is preferred. Further, when two or more exist, generally, any two of the interfering groups (excluding phenylene) do not directly bond to each other. Herein, by "interfered" or "interfering", it means that the interfering group enters the main molecular chain of the alkylene, alkenylene or alkynylene, whereby constituting a part of the main chain, positions appropriate to this interfering including the inside and either end of the molecular chain. For example, the group —$CH_2$—$CH_2$—$CH_2$—$CH_2$— after interfered by one phenylene group, will result in —$CH_2$-phenylene-$CH_2$—$CH_2$—$CH_2$—, —$CH_2$—$CH_2$-phenylene-$CH_2$—$CH_2$—, —$CH_2$—$CH_2$—$CH_2$-phenylene-$CH_2$—, —$CH_2$—$CH_2$—$CH_2$—$CH_2$-phenylene- or -phenylene-$CH_2$—$CH_2$—$CH_2$—$CH_2$—.

According to this invention, the

is preferably selected from an organic carrier and an inorganic carrier, more preferably an inorganic carrier. These carriers could be used with one kind or as a mixture of two or more kinds.

According to this invention, as the organic carrier, olefin homopolymers or copolymers, vinyl alcohol homopolymers or copolymers, cyclodextrins, polyesters or co-polyesters, polyamides or co-polyamides, vinyl chloride homopolymers or copolymers, acrylic homopolymers or copolymers, methacrylic homopolymers or copolymers, styrene homopolymers or copolymers, and partly crosslinked products of these homopolymers or copolymers can be exemplified, preferably partly crosslinked styrene polymers (for example one having a crosslinking degree of from 2% to less than 100%). These organic carriers could be used with one kind or as a mixture of two or more kinds. According to this invention, as the inorganic carrier, a refractory oxide of a Group IIA, IIIA, IVA or IVB metal in the Periodic Table of Elements (for example silica, alumina, magnesia, titania, zirconia, or thorium oxide), or a refractory composite oxide of any two or more of these metals (for example, silica-alumina, magnesia-alumina, titania-silica, titania-magnesia, or titania-alumina), and clay, zeolite (for example SBA-15, MCM-41, MCF, HMS, KIT-6 or SBA-16), mica, montmorillonite, bentonite or kieselguhr can be exemplified. These inorganic carriers could be used with one kind or as a mixture of two or more kinds.

As the inorganic carrier, more preference is given to one or more selected from the group consisting of silica, zeolite (preferably SBA-15, MCM-41, MCF, HMS, KIT-6 or SBA-16) and kieselguhr.

According to this invention, the average value n is preferably such that the ratio by weight of the quaternary phosphonium group to the carrier will be 1 to 20:80 to 99.

According to this invention, the elution loss D of the supported quaternary phosphonium catalyst is less than 2%, preferably less than 1.5%, more preferably less than 1%, more preferably less than 0.8%, further more preferably less than 0.5%. In view of this, in the supported quaternary phosphonium catalyst according to this invention, the catalyst active components (the quaternary phosphonium groups) bond with the carrier strongly and firmly, not easy to detach therefrom, which results in a constant and stable performance of the catalyst.

According to this invention, the elution loss D is determined according to a method comprising steps of: weighting 2 g of the supported quaternary phosphonium catalyst with a P content of P1 (unit: wt %), (1) suspending the supported quaternary phosphonium catalyst in 40 ml methanol, stirring (at a stirring speed of 100 rpm) the resultant at 100° C. for 4 h, then immediately filtering the resultant so as to separate the supported quaternary phosphonium catalyst, (2) then, suspending the separated supported quaternary phosphonium catalyst in 40 ml methanol, stirring (at a stirring speed of 100 rpm) the resultant at 100° C. for 4 h, then immediately filtering the resultant so as to separate the supported quaternary phosphonium catalyst, repeating the process (2) for further 10 times, and then determining the P content of the finally separated supported quaternary phosphonium catalyst as P2 (unit: wt %), and then calculating the elution loss D as follows.

$$D=(P1-P2)/P1\times100\%$$

According to this invention, the P content can be determined by a XRF method. For example, this determination can be conducted on the S4 PIONEER X-ray fluorescence spectrometer (produced by the Bruker company) with a standardless and semi-quantitative process.

According to this invention, the supported quaternary phosphonium catalyst can be produced for example by the following process.

According to this invention, the process comprises a step of reacting a tertiary phosphine of the following formula (2) with a macromolecular agent of the following formula (3).

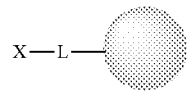

(2)

wherein $R_1$, $R_2$ and $R_3$ are different from or identical to each other, and are each independently selected from the group consisting of an optionally substituted $C_{1-20}$ straight-chain or branched alkyl, an optionally substituted $C_{2-20}$ straight-chain or branched alkenyl, an optionally substituted $C_{2-20}$ straight-chain or branched alkynyl, an optionally substituted $C_{3-20}$ cycloalkyl or an optionally substituted $C_{6-20}$ aryl, ⎯ represents a covalent bond.

(3)

wherein X is a halogen atom, L is a bivalent bonding group,

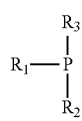

is a carrier, ⎯ represents a covalent bond.

According to this invention, the reaction could be conducted in the presence of a solvent. As the reaction solvent, any chemical inert solvent which can dissolve the tertiary phosphine can be exemplified, for example a nitrile based solvent for example acetonitrile or benzonitrile, with benzonitrile more preferred. These solvents could be used with one kind or as a mixture of two or more kinds.

According to this invention, to carry out the reaction, the reaction temperature could be 100 to 190° C., preferably 120 to 190° C., and the reaction duration could be 10 to 40 h, preferably 10 to 30 h.

According to this invention, to carry out the reaction, the ratio by weight of the tertiary phosphine to the macromolecular agent could be 1 to 20:80 to 99, preferably 1 to 15:85 to 99.

According to this invention, upon completion of the reaction, by a separation process normally known in this field, it is easy to separate the supported quaternary phosphonium catalyst from the reaction mixture. As the separation process, filtration, washing (for example washing with the reaction solvent, ethanol or acetone for 2-6 times, 2-5 times, 2-4 times, or 2-3 times) and drying (for example drying under vacuum at 60 to 100° C. for 4-20 h) can be exemplified, but without limiting thereto.

According to this invention, the X preferably Cl, Br or I, more preferably Br or I.

According to this invention, preferably the $R_1$, $R_2$ and $R_3$ are different from or identical to each other, are each independently selected from the group consisting of a $C_{2-10}$ straight-chain or branched alkyl, a $C_{2-10}$ straight-chain or branched alkyl substituted by one or more (for example 1-4, 1-3, 1-2 or 1) phenyl or $C_{3-20}$ cycloalkyl, a $C_{2-10}$ straight-chain or branched alkenyl (for example allyl), a $C_{2-10}$ straight-chain or branched alkenyl substituted by one or more (for example 1-4, 1-3, 1-2 or 1) phenyl or $C_{3-20}$ cycloalkyl, a $C_{3-20}$ cycloalkyl, a $C_{3-20}$ cycloalkyl substituted by one or more (for example 1-4, 1-3, 1-2 or 1) $C_{1-6}$ straight-chain or branched alkyl or $C_{2-6}$ straight-chain or branched alkenyl, a $C_{6-20}$ aryl (for example phenyl) or a $C_{6-20}$ aryl substituted by one or more (for example 1-4, 1-3, 1-2 or 1) $C_{1-6}$ straight-chain or branched alkyl or $C_{2-6}$ straight-chain or branched alkenyl.

According to this invention, the L is preferably selected from the group consisting of an optionally substituted $C_{1-20}$ straight-chain or branched alkylene, an optionally substituted $C_{2-20}$ straight-chain or branched alkenylene or an optionally substituted $C_{2-20}$ straight-chain or branched alkynylene.

According to this invention, the L is more preferably selected from the group consisting of a $C_{1-20}$ straight-chain or branched alkylene, more preferably a $C_{2-8}$ straight-chain alkylene.

According to this invention, the alkylene, alkenylene or alkynylene in said L may be optionally interfered by one or more (for example one to three, one to two, or one) interfering group selected from the group consisting of —O—, —S—, —NR$_a$— (R$_a$ is a C$_{1-4}$ alkyl) and phenylene at any appropriate position. As the interfering group, phenylene is preferred. Further, when two or more exist, generally, any two of the interfering groups (excluding phenylene) do not directly bond to each other. Herein, by "interfered" or "interfering", it means that the interfering group enters the main molecular chain of the alkylene, alkenylene or alkynylene, whereby constituting a part of the main chain, positions appropriate to this interfering including the inside and either end of the molecular chain. For example, the group —CH$_2$—CH$_2$—CH$_2$—CH$_2$— after interfered by one phenylene group, will result in —CH$_2$-phenylene-CH$_2$—CH$_2$—CH$_2$—, —CH$_2$—CH$_2$-phenylene-CH$_2$—CH$_2$—, —CH$_2$—CH$_2$—CH$_2$-phenylene-CH$_2$—, —CH$_2$—CH$_2$—CH$_2$—CH$_2$-phenylene- or -phenylene-CH$_2$—CH$_2$—CH$_2$—CH$_2$—.

According to this invention, the

is preferably selected from an organic carrier and an inorganic carrier, more preferably an inorganic carrier. These carriers could be used with one kind or as a mixture of two or more kinds.

According to this invention, as the organic carrier, olefin homopolymers or copolymers, vinyl alcohol homopolymers or copolymers, cyclodextrins, polyesters or co-polyesters, polyamides or co-polyamides, vinyl chloride homopolymers or copolymers, acrylic homopolymers or copolymers, methacrylic homopolymers or copolymers, styrene homopolymers or copolymers, and partly crosslinked products of these homopolymers or copolymers can be exemplified, preferably partly crosslinked styrene polymers (for example one having a crosslinking degree of from 2% to less than 100%). These organic carriers could be used with one kind or as a mixture of two or more kinds.

According to this invention, as the inorganic carrier, a refractory oxide of a Group IIA, IIIA, IVA or IVB metal in the Periodic Table of Elements (for example silica, alumina, magnesia, titania, zirconia, or thorium oxide), or a refractory composite oxide of any two or more of these metals (for example, silica-alumina, magnesia-alumina, titania-silica, titania-magnesia, or titania-alumina), and clay, zeolite (for example SBA-15, MCM-41, MCF, HMS, KIT-6 or SBA-16), mica, montmorillonite, bentonite or kieselguhr can be exemplified. These inorganic carriers could be used with one kind or as a mixture of two or more kinds.

As the inorganic carrier, more preference is given to one or more selected from the group consisting of silica, zeolite (preferably SBA-15, MCM-41, MCF, HMS, KIT-6 or SBA-16) and kieselguhr.

According to this invention, the macromolecular agent can be produced by reacting the carrier with a halogenation agent of the following formula (4).

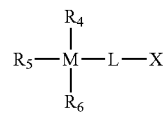

(4)

wherein X is a halogen atom, L is a bivalent bonding group, M is Ti, Si or Zr, preferably Si, R$_4$, R$_5$ and R$_6$ are different from or identical to each other, and are each independently selected from the group consisting of a C$_{1-4}$ straight-chain or branched alkoxy, preferably methoxy or ethoxy.

According to this invention, the X preferably Cl, Br or I, more preferably Cl herein.

According to this invention, the L is preferably selected from the group consisting of an optionally substituted C$_{1-20}$ straight-chain or branched alkylene, an optionally substituted C$_{2-20}$ straight-chain or branched alkenylene or an optionally substituted C$_{2-20}$ straight-chain or branched alkynylene.

According to this invention, the L is more preferably selected from the group consisting of a C$_{1-20}$ straight-chain or branched alkylene, more preferably a C$_{2-8}$ straight-chain alkylene.

According to this invention, the alkylene, alkenylene or alkynylene in said L may be optionally interfered by one or more (for example one to three, one to two, or one) interfering group selected from the group consisting of —O—, —S—, —NR$_a$— (R$_a$ is a C$_{1-4}$ alkyl) and phenylene at any appropriate position. As the interfering group, phenylene is preferred. Further, when two or more exist, generally, any two of the interfering groups (excluding phenylene) do not directly bond to each other. Herein, by "interfered" or "interfering", it means that the interfering group enters the main molecular chain of the alkylene, alkenylene or alkynylene, whereby constituting a part of the main chain, positions appropriate to this interfering including the inside and either end of the molecular chain. For example, the group —CH$_2$—CH$_2$—CH$_2$—CH$_2$— after interfered by one phenylene group, will result in —CH$_2$-phenylene-CH$_2$—CH$_2$—CH$_2$—, —CH$_2$—CH$_2$-phenylene-CH$_2$—CH$_2$—, —CH$_2$—CH$_2$—CH$_2$-phenylene-CH$_S$, —CH$_2$—CH$_2$—CH$_2$—CH$_2$-phenylene- or -phenylene-CH$_2$—CH$_2$—CH$_2$—CH$_2$—.

According to this invention, to carry out the reaction, the reaction temperature could be 70 to 140° C., preferably 90 to 120° C., and the reaction duration could be 1 to 60 h, preferably 5 to 48 h.

According to this invention, to carry out the reaction, the ratio by weight of the halogenation agent to the carrier could be 0.005 to 0.15:1, preferably 0.01 to 0.1:1. According to this invention, the reaction could be conducted in the presence of a solvent. As the reaction solvent, any chemical inert solvent that can dissolve the halogenation agent could be exemplified, for example a C$_{6-12}$ aromatic hydrocarbon or a halogenated C$_{6-12}$ aromatic hydrocarbon. Specifically, toluene, xylene, trimethyl benzene, ethyl benzene, diethyl benzene, chlorinated toluene, chlorinated ethyl benzene, brominated toluene, brominated ethyl benzene could be exemplified. Preference is given to the C$_{6-12}$ aromatic hydrocarbon or toluene. These solvents could be used with one kind or as a mixture of two or more kinds.

According to this invention, the

is preferably an organic carrier or an inorganic carrier, more preferably an inorganic carrier. These carriers could be used with one kind or as a mixture of two or more kinds.

According to this invention, as the organic carrier, olefin homopolymers or copolymers, vinyl alcohol homopolymers or copolymers, cyclodextrins, polyesters or co-polyesters, polyamides or co-polyamides, vinyl chloride homopolymers or copolymers, acrylic homopolymers or copolymers, methacrylic homopolymers or copolymers, styrene homopolymers or copolymers, and partly crosslinked products of these homopolymers or copolymers can be exemplified, preferably partly crosslinked styrene polymers (for example one having a crosslinking degree of from 2% to less than 100%). These organic carriers could be used with one kind or as a mixture of two or more kinds. According to this invention, as the inorganic carrier, a refractory oxide of a Group IIA, IIIA, IVA or IVB metal in the Periodic Table of Elements (for example silica, alumina, magnesia, titania, zirconia, or thorium oxide), or a refractory composite oxide of any two or more of these metals (for example, silica-alumina, magnesia-alumina, titania-silica, titania-magnesia, or titania-alumina), and clay, zeolite (for example SBA-15, MCM-41, MCF, HMS, KIT-6 or SBA-16), mica, montmorillonite, bentonite or kieselguhr can be exemplified. These inorganic carriers could be used with one kind or as a mixture of two or more kinds.

As the inorganic carrier, more preference is given to one or more selected from the group consisting of silica, zeolite (preferably SBA-15, MCM-41, MCF, HMS, KIT-6 or SBA-16) and kieselguhr.

According to this invention, suitable silica can be produced by any conventional process, or is any commercially available one.

According to this invention, the specific surface area (by a BET process) of the carrier could be 100 to 1500 $m^2/g$, preferably 200 to 1000 $m^2/g$, while the average particle size (measured by a laser particle size analyzer) thereof could be 1 to 500 mm, preferably 1 to 100 mm. According to this invention, the carrier can present in any form, for example, fine powder, particulate, sphere, aggregate, or other forms.

According to this invention, as the carrier, the inorganic carrier is preferred. Generally, an inorganic carrier carries active functional groups like hydroxyl groups on its surface. By reacting these active functional groups with the alkoxy groups on the halogenation agent, the macromolecular agent could be produced.

According to one embodiment of this invention, the inorganic carrier could be subjected to a thermal activation before use so as to enhance or modify the activity of these active functional groups. The thermal activation can be conducted in a normal way. For example, the inorganic carrier is treated by heat under a reduced pressure or under an inert gas atmosphere. By an inert gas atmosphere herein, it means that there exists no component capable of reacting with the inorganic carrier in the gas atmosphere, or if does exist, only at a rather minor amount. As the inert gas atmosphere, a nitrogen gas or rare gas atmosphere can be exemplified, preferably a nitrogen gas atmosphere. Generally, the temperature at which the thermal activation is conducted is from 200 to 800° C., preferably 400-700° C., preferably 400-650° C., while the duration for the thermal activation is from 0.5 to 24 hours, preferably 2 to 12 hours, preferably 4 to 8 hours. According to this invention, as the carrier, an organic carrier carrying active functional groups like a hydroxyl group, an amino group, a sulfo group, or a carboxylic group on its surface can be used as well. In this connection, vinyl alcohol homopolymers or copolymers, cyclodextrins, polyesters or co-polyesters, polyamides or co-polyamides, acrylic homopolymers or copolymers, or methacrylic homopolymers or copolymers can be exemplified. By reacting these active functional groups with the alkoxy groups on the halogenation agent, the macromolecular agent could be produced as well.

According to one embodiment of this invention, the organic carrier could be subjected to a thermal activation before use so as to enhance or modify the activity of these active functional groups. The thermal activation can be conducted in a normal way. For example, the organic carrier is treated by heat under a reduced pressure or under an inert gas atmosphere. By an inert gas atmosphere herein, it means that there exists no component capable of reacting with the organic carrier in the gas atmosphere, or if does exist, only at a rather minor amount. As the inert gas atmosphere, a nitrogen gas or rare gas atmosphere can be exemplified, preferably a nitrogen gas atmosphere. In view of the poor heat resistance, the thermal activation in connection with the organic carrier should be conducted with the proviso that the inherent structure and composition of the organic carrier will not be destroyed. Generally, the temperature at which the thermal activation is conducted is from 50 to 400° C., preferably 100-250° C., while the duration for the thermal activation is from 1 to 24 hours, preferably 2 to 12 hours. According to this invention, as the macromolecular agent of the formula (3), a halogen-containing organic carrier could be used as such, for example homopolymers of a halogen-containing monomer (for example vinyl chloride or chloro styrene) or copolymers of the halogen-containing monomer with a comonomer (for example ethylene, propylene, styrene or (meth)acrylic ester), and partly crosslinked products of these homopolymers or copolymers can be exemplified. At this time, the group X-L- is provided by the halogen-containing organic carrier per se. Further, the macromolecular agent of the formula (3) can also be produced by halogenating a halogen-free organic carrier. As the halogen-free organic carrier, for example olefin homopolymers or copolymers, styrene homopolymers or copolymers, and partly crosslinked products of these homopolymers or copolymers can be exemplified, especially partly crosslinked styrene polymers (for example one having a crosslinking degree of from 2% to less than 100%). The process for halogenating (especially chlorinating) the halogen-free organic carrier has been well known in the polymer field. For example, a suspension chlorination process or a solution chlorination process can be exemplified, further description thereon omitted herein. By halogenation, a halo group (for example a chloroalkyl group) can be introduced into the halogen-free organic carrier. At this time, the group X-L- is provided by the halo group.

According to this invention, upon completion of the reaction, by a separation process normally known in this field, it is easy to separate the macromolecular agent from the reaction mixture. As the separation process, filtration, washing (for example washing with the reaction solvent, ethanol or methanol for 2-6 times, 2-5 times, 2-4 times, or 2-3 times) and drying (for example drying at 80 to 150° C. for 4-20 h) can be exemplified, but without limiting thereto.

According to this invention, when X is Cl, if needed, part or whole amount of Cl could be replaced by Br or I. To this end, the aforesaid process further optionally comprises a step of contacting the macromolecular agent with one or more modifying agent selected from the group consisting of a bromination agent and an iodization agent for one or more time(s) (for example 2 to 5 times, 2 to 4 times, 2 to 3 times or 2 times), before reacting the macromolecular agent with the tertiary phosphine.

According to this invention, for the contacting reaction (a single contacting), the reaction duration could be 1 to 4 h, preferably 1.5 to 4 h, and the reaction temperature could be 20-100° C., preferably the normal temperature.

According to this invention, for the contacting reaction (a single contacting), the ratio by weight of the modifying agent to the macromolecular agent could be 0.01 to preferably 0.02 to 0.6:1.

According to this invention, the contacting reaction could be conducted in the presence of a solvent. As the reaction solvent, water, alcohols, amides or ketones can be exemplified, with the only proviso that the solvent facilitates the reaction between the modifying agent and the macromolecular agent and is chemically inert, which is obvious to a person skilled in the art.

According to this invention, upon completion of all the contacting reactions, by a separation process normally known in this field, it is easy to separate the product (the modified macromolecular agent) from the reaction mixture. As the separation process, filtration, washing (for example washing with the reaction solvent, water or methanol for 2-6 times, 2-5 times, 2-4 times, or 2-3 times) and drying (for example drying under vacuum at 60 to 100° C. for 4-20 h) can be exemplified, but without limiting thereto.

According to this invention, as the bromination agent, an alkali metal bromide could be exemplified, for example one or more selected from the group consisting of LiBr, NaBr, KBr and CsBr. As the iodization agent, an alkali metal iodide could be exemplified, for example one or more selected from the group consisting of LH, NaI, KI and CsI. These bromination agents or iodization agents could be provided in the form of a solution (especially in water).

By the aforesaid process, a/the supported quaternary phosphonium catalyst could be produced.

According to this invention, the aforesaid supported quaternary phosphonium catalyst can be easily regenerated if its catalyst activity decreases to an unacceptable level after use. As the regeneration process, a process comprising a step of reacting the tertiary phosphine of the formula (2) with the spent supported quaternary phosphonium catalyst can be exemplified. To this end, the process for producing a supported quaternary phosphonium catalyst according to this invention can be used, with the only exception that part or whole amount of the macromolecular agent be directly replaced by the spent supported quaternary phosphonium catalyst, whereby regenerating the supported quaternary phosphonium catalyst.

According to this invention, any of the aforesaid supported quaternary phosphonium catalysts can be used as the catalyst in producing dialkyl carbonates by a transesterification process. Then, according to a further embodiment of this invention, this invention further relates to process for producing a dialkyl carbonate, comprising a step of contacting a $C_{2-10}$ alkylene carbonate with a monohydric $C_{1-10}$ alkanol in the presence of this supported quaternary phosphonium catalyst, to produce (co-produce) a di-$C_{1-10}$alkyl carbonate and a $C_{2-10}$ alkanediol.

According to this invention, as the $C_{2-10}$ alkylene carbonate, a $C_{2-5}$ alkylene carbonate is preferred, ethylene carbonate or propylene carbonate is most preferred.

According to this invention, as the monohydric $C_{1-10}$ alkanol, a monohydric $C_{1-3}$ alkanol is preferred, methanol is most preferred.

According to this invention, by contacting ethylene carbonate (propylene carbonate) with methanol in the presence of the supported quaternary phosphonium catalyst, it is possible to co-produce dimethyl carbonate and ethylene glycol (propylene glycol) with a high yield.

According to this invention, the contacting could be conducted under conditions normally known in this field in the manner normally known in this field. For example, the reaction temperature could be 60 to 140° C., preferably 80 to 140° C., the reaction duration could be 0.1 to 20 h, preferably 1 to 10 h, but not limiting thereto. Further, for the contacting, the reaction pressure could be a normal pressure or an elevated pressure (for example an autogenic pressure of the reactor or 0.2-1.5 MPa), but not limiting thereto.

According to this invention, for the contacting, the ratio by mol of the monohydric $C_{1-10}$ alkanol to the $C_{2-10}$ alkylene carbonate could be 2 to 10:1, preferably 2 to 6:1, and the ratio by weight of the supported quaternary phosphonium catalyst to the $C_{2-10}$ alkylene carbonate could be 0.005 to 0.5:1, preferably 0.01 to 0.2:1.

EXAMPLE

The present invention is further illustrated by using the following examples, but not limiting to same.

Example 1

10.0 g carrier (Aerisol 200 produced by Degussa, with a specific surface area of 210 m$^2$/g) was placed into a 500 mL three-necked bottle, and then 200 mL anhydrous toluene and 2.0 g γ-chloropropyl triethoxy silane (CPTES, with a molecular structure of $C_3H_6ClSi(OC_2H_5)_3$) were added thereto, after refluxed at 110° C. for 24 h, filtrated, washed with anhydrous ethanol for 3 times, and then oven-dried at 110° C. for 2 h, to obtain a macromolecular agent.

Then, the obtained macromolecular agent was added to a solution of 2.0 g triphenylphosphine in 100 mL benzonitrile, after reacting at 190° C. for 40 h, filtrated, washed respectively by ethanol and acetone for three times, and vacuum dried at 60° C. for 12 h, a supported quaternary phosphonium catalyst was obtained.

Examples 2 to 9

The same as Example 1, with the only exception that the nature and the amount of the carrier, the nature and the amount of the halogenation agent, the reaction temperature and the reaction duration for producing the macromolecular agent, the nature and the amount of the tertiary phosphine, and the reaction temperature and the reaction duration for producing the supported quaternary phosphonium catalyst were changed as shown in the Table 1.

TABLE 1

| Macro-molecular agent No. | Carrier | | Halogenation agent | | Reaction temperature, °C. | Reaction duration, h |
|---|---|---|---|---|---|---|
| | Nature | Specific surface area, m²/g | Amount, g | Nature | Amount, g | | |
| A1 | Aerosil 200 | 210 | 10.0 | CPTES | 2.0 | 110 | 24 |
| A2 | Aerosil 200 | 210 | 10.0 | CPTES | 2.0 | 110 | 24 |
| A3 | SBA-15 | 752 | 10.0 | CPTES | 3.0 | 120 | 24 |
| A4 | MCM-41 | 1098 | 10.0 | CPTMS[a] | 3.0 | 80 | 58 |
| A5 | MCF | 653 | 10.0 | CPTMS | 2.0 | 120 | 24 |
| A6 | MCF | 653 | 10.0 | CPTMS | 2.0 | 120 | 24 |
| A7 | MCF | 653 | 10.0 | CBTES[b] | 2.0 | 120 | 24 |
| A8 | HMS | 741 | 10.0 | CBTES | 2.0 | 120 | 3 |
| A9 | HMS | 741 | 10.0 | CBTES | 2.0 | 120 | 24 |

| Example No. | Tertiary phosphine | | Reaction duration, h | Reaction temperature, °C. | Macro-moleculer agent |
|---|---|---|---|---|---|
| | Nature | Amount, g | | | |
| 1 | Triphenylphosphine | 2.0 | 40 | 190 | A1 |
| 2 | Triphenylphosphine | 0.2 | 40 | 190 | A2 |
| 3 | Triphenylphosphine | 2.0 | 40 | 190 | A3 |
| 4 | Trioctylphosphine | 2.0 | 30 | 190 | A4 |
| 5 | Phenyldicyclohexyl-phosphine | 2.0 | 30 | 170 | A5 |
| 6 | Triethylphosphine | 1.5 | 10 | 100 | A6 |
| 7 | Allyldiphenylphosphine | 0.3 | 20 | 150 | A7 |
| 8 | Tributylphosphine | 2.0 | 20 | 120 | A8 |
| 9 | Tri(2-tolyl)phosphine | 2.0 | 40 | 190 | A9 |

[a]3-chloropropyl trimethoxy silane, with a molecular structure of $ClC_3H_6Si(OCH_3)_3$;
[b]4-chloromethyl phenyl triethoxy silane, with a molecular structure of $ClCH_2C_6H_4Si(OC_2H_5)_3$.

Example 10

5.0 g of the supported quaternary phosphonium catalyst produced by Example 1 was placed into 100 ml NaBr solution (0.5 mol/L), stood at the normal temperature for an exchanging duration of 2 h, after filtration, the obtained solid was further placed into 100 ml NaBr solution (0.5 mol/L), stood at the normal temperature for an exchanging duration of 2 h, after filtration, a supported quaternary phosphonium catalyst was obtained.

Example 11

The same as Example 10, except that for each time, 100 ml NaBr solution (0.5 mol/L) was changed to 100 ml KI solution (0.5 mol/L) and the exchanging duration was changed to 4 h, to obtain a supported quaternary phosphonium catalyst.

Examples 12 to 22

22.0 g ethylene carbonate, 32.0 g methanol and 1.1 g of a supported quaternary phosphonium catalyst produced according to any of Examples 1 to 11 were placed into a 100 ml autoclave (with the ratio by mol of methanol to ethylene carbonate of 4:1, and the ratio by weight of the supported quaternary phosphonium catalyst to ethylene carbonate of 0.05:1), reacted at 100° C. for 4 h. Upon completion of the reaction, the autoclave was cooled down to the room temperature and evacuated. The liquid phase was sampled and subject to a gas chromatography analysis, and the result was listed in the following Table 2, together with the elution loss D (%) determined for each catalyst.

TABLE 2

| Example No. | Catalyst No. | Ethylene carbonate conversion, % | Dimethyl carbonate selectivity, % | Ethylene glycol selectivity, % | Elution loss D, % |
|---|---|---|---|---|---|
| 12 | Example 1 | 49.2 | 98.9 | 98.7 | 0.2 |
| 13 | Example 2 | 5.6 | 96.3 | 95.8 | 0.5 |
| 14 | Example 3 | 47.5 | 96.7 | 95.9 | 0.6 |
| 15 | Example 4 | 41.5 | 97.1 | 96.5 | 0.3 |
| 16 | Example 5 | 39.3 | 95.4 | 96.1 | 0.5 |
| 17 | Example 6 | 23.1 | 94.9 | 95.2 | 1.0 |
| 18 | Example 7 | 9.5 | 95.6 | 94.4 | 0.9 |
| 19 | Example 8 | 32.1 | 97.5 | 96.1 | 0.8 |
| 20 | Example 9 | 48.2 | 96.3 | 95.6 | 0.8 |
| 21 | Example 10 | 45.6 | 96.5 | 94.3 | 0.9 |
| 22 | Example 11 | 46.2 | 98.9 | 97.1 | 1.2 |

Example 23

The same as Example 12, with the only exception that reaction temperature was changed to 120° C. The result is that, the ethylene carbonate conversion was 50.1%, the dimethyl carbonate selectivity was 95.6%, the ethylene glycol selectivity was 94.5%.

Example 24

The same as Example 12, with the only exception that reaction temperature was changed to 140° C. The result is that, the ethylene carbonate conversion was 53.5%, the dimethyl carbonate selectivity was 92.5%, the ethylene glycol selectivity was 91.9%.

Example 25

The same as Example 12, with the only exception that reaction temperature was changed to 80° C. The result is that, the ethylene carbonate conversion was 25.6%, the dimethyl carbonate selectivity was 98.5%, the ethylene glycol selectivity was 99.1%.

Example 26

The same as Example 12, with the only exception that the amount of methanol to be used was changed to 48 g (the ratio by mol of methanol to ethylene carbonate was 6:1). The result is that, the ethylene carbonate conversion was 50.5%, the dimethyl carbonate selectivity was 97.1%, the ethylene glycol selectivity was 96.5%.

Example 27

The same as Example 12, with the only exception that the amount of methanol to be used was changed to 16.0 g (the ratio by mol of methanol to ethylene carbonate was 2:1). The result is that, the ethylene carbonate conversion was 32.1%, the dimethyl carbonate selectivity was 96.7%, the ethylene glycol selectivity was 97.1%.

Example 28

The same as Example 12, with the only exception that the amount of the supported quaternary phosphonium catalyst to be used was changed to 0.55 g (the ratio by weight of the supported quaternary phosphonium catalyst to ethylene carbonate was 0.025:1). The result is that, the ethylene carbonate conversion was 35.1%, the dimethyl carbonate selectivity was 97.1%, the ethylene glycol selectivity was 96.8%.

Example 29

The same as Example 12, with the only exception that the amount of the supported quaternary phosphonium catalyst to be used was changed to 2.2 g (the ratio by weight of the supported quaternary phosphonium catalyst to ethylene carbonate was 0.1:1). The result is that, the ethylene carbonate conversion was 51.1%, the dimethyl carbonate selectivity was 93.4%, the ethylene glycol selectivity was 92.2%.

Example 30

The same as Example 12, with the only exception that the amount of the supported quaternary phosphonium catalyst to be used was changed to 4.4 g (the ratio by weight of the supported quaternary phosphonium catalyst to ethylene carbonate was 0.2:1). The result is that, the ethylene carbonate conversion was 52.3%, the dimethyl carbonate selectivity was 93.2%, the ethylene glycol selectivity was 92.8%.

Example 31

Example 12 was repeated for 12 times, with the only exception that from the second time, a spent catalyst resulted from the previous time was used as the supported quaternary phosphonium catalyst, the results were shown in Table 3. As can be seen from Table 3, after the supported quaternary phosphonium catalyst according to this invention has been recycled for 12 times, the catalyst activity (in terms of ethylene carbonate conversion) decreases less than 5%.

TABLE 3

| Recycling times | Ethylene carbonate conversion, % | Dimethyl carbonate selectivity, % | Ethylene glycol selectivity, % |
|---|---|---|---|
| 1 | 49.2 | 98.9 | 98.7 |
| 2 | 49.0 | 98.5 | 98.6 |
| 3 | 48.6 | 99.0 | 98.5 |
| 4 | 49.0 | 98.1 | 99.0 |
| 5 | 48.5 | 99.1 | 98.5 |
| 6 | 48.6 | 99.2 | 99.0 |
| 7 | 48.4 | 99.1 | 98.7 |
| 8 | 48.2 | 98.9 | 98.8 |
| 9 | 48.1 | 98.4 | 98.5 |
| 10 | 47.8 | 99.2 | 98.8 |
| 11 | 48.0 | 99.1 | 98.5 |
| 12 | 47.5 | 99.0 | 98.4 |

Example 32

10.0 g carrier (SG-5 polyvinylchloride, having a K value of 68-66 and an averaged polymerization degree of 1135-981, produced by Aladdin Reagents (Shanghai) Co., Ltd.) was placed into a 500 mL three-necked bottle, which contained a solution of 2.0 g triphenylphosphine in 100 mL benzonitrile, after reacting at 190° C. for 40 h, filtrated, washed respectively by ethanol and acetone for three times, and vacuum dried at 60° C. for 12 h, a supported quaternary phosphonium catalyst was obtained.

22.0 g ethylene carbonate, 32.0 g methanol and 1.1 g of the supported quaternary phosphonium catalyst were placed into a 100 ml autoclave (with the ratio by mol of methanol to ethylene carbonate of 4:1, and the ratio by weight of the supported quaternary phosphonium catalyst to ethylene carbonate of 0.05:1), and reacted at 100° C. for 4 h. Upon completion of the reaction, the autoclave was cooled down to the room temperature and evacuated. The liquid phase was sampled and subject to a gas chromatography analysis. The result is that, the ethylene carbonate conversion was 25.1%, the dimethyl carbonate selectivity was 98.2%, the ethylene glycol selectivity was 98.5%, and the elution loss D (%) determined was 0.5%.

Example 33

10.0 g carrier (chloromethylated crosslinked polystyrene resin, having a Cl content of 19.2 wt %, and a crosslinking degree of 5.8%, produced by Jiangsu Suqing Water Treatment Engineering Group Co., Ltd) was placed into a 500 mL three-necked bottle, which contained a solution of 2.0 g triphenylphosphine in 100 mL benzonitrile, after reacting at 190° C. for 40 h, filtrated, washed respectively by ethanol and acetone for three times, and vacuum dried at 60° C. for 12 h, a supported quaternary phosphonium catalyst was obtained.

22.0 g ethylene carbonate, 32.0 g methanol and 1.1 g of the supported quaternary phosphonium catalyst were placed into a 100 ml autoclave (with the ratio by mol of methanol to ethylene carbonate of 4:1, and the ratio by weight of the supported quaternary phosphonium catalyst to ethylene carbonate of 0.05:1), and reacted at 100° C. for 4 h. Upon completion of the reaction, the autoclave as cooled down to the room temperature and evacuated. The liquid phase was sampled and subject to a gas chromatography analysis. The result is that, the ethylene carbonate conversion was 39.1%, the dimethyl carbonate selectivity was 98.5%, the ethylene glycol selectivity was 98.3%, and the elution loss D (%) determined was 0.4%.

Example 34

10.0 g carrier (Montmorillonite K-10, produced by J&K Scientific Ltd., with a specific surface area of 242 m$^2$/g) was placed into a 500 mL three-necked bottle, and then 200 mL anhydrous toluene and 2.0 g γ-chloropropyl triethoxy silane (CPTES, with a molecular structure of $C_3H_6ClSi(OC_2H_5)_3$) were added thereto, after refluxed at 110° C. for 24 h, filtrated, washed with anhydrous ethanol for 3 times, and then oven-dried at 110° C. for 12 h, to obtain a macromolecular agent.

Then, the obtained macromolecular agent was added to a solution of 2.0 g triphenylphosphine in 100 mL benzonitrile, after reacting at 190° C. for 40 h, filtrated, washed respectively by ethanol and acetone for three times, and vacuum dried at 60° C. for 12 h, a supported quaternary phosphonium catalyst was obtained.

22.0 g ethylene carbonate, 32.0 g methanol and 1.1 g of the supported quaternary phosphonium catalyst were placed into a 100 ml autoclave (with the ratio by mol of methanol to ethylene carbonate of 4:1, and the ratio by weight of the supported quaternary phosphonium catalyst to ethylene carbonate of 0.05:1), and reacted at 100° C. for 4 h. Upon completion of the reaction, the autoclave was cooled down to the room temperature and evacuated. The liquid phase was sampled and subject to a gas chromatography analysis. The result is that, the ethylene carbonate conversion was 18.7%, the dimethyl carbonate selectivity was 86.9%, the ethylene glycol selectivity was 94.2%, and the elution loss D (%) determined was 0.8%.

Example 35

Comparative Example 10.0 g carrier (Montmorillonite K-10, produced by J&K Scientific Ltd., with a specific surface area of 242 m$^2$/g) was dispersed into a solution of 3.0 g methyltriphenylphosphine chloride in 100 mL water, after stirred at 80° C. till dry, the resultant was vacuum dried at 100° C., a catalyst was obtained.

22.0 g ethylene carbonate, 32.0 g methanol and 1.1 g of the catalyst were placed into a 100 ml autoclave (with the ratio by mol of methanol to ethylene carbonate of 4:1, and the ratio by weight of the catalyst to ethylene carbonate of 0.05:1), and reacted at 100° C. for 4 h. Upon completion of the reaction, the autoclave was cooled down to the room temperature and evacuated. The liquid phase was sampled and subject to a gas chromatography analysis. The result is that, the ethylene carbonate conversion was 25.4%, the dimethyl carbonate selec-tivity was 95.6%, the ethylene glycol selectivity was 94.8%, and the elution loss D (%) determined was 25%.

Example 36

25.7 g propylene carbonate, 32.0 g methanol and 1.1 g of the supported quaternary phosphonium catalyst produced by Example 1 were placed into a 100 ml autoclave (with the ratio by mol of methanol to propylene carbonate of 4:1, and the ratio by weight of the supported quaternary phosphonium catalyst to propylene carbonate of 0.05:1), and reacted at 100° C. for 4 h. Upon completion of the reaction, the autoclave was cooled down to the room temperature and evacuated. The liquid phase was sampled and subject to a gas chromatography analysis. The result is that, the propylene carbonate conversion was 45.2%, the dimethyl carbonate selectivity was 98.9%, the propylene glycol selectivity was 98.8%.

Example 37

10.0 g carrier (Aerisol 200 produced by Degussa, with a specific surface area of 210 m$^2$/g) was placed into a 500 mL three-necked bottle, and then 200 mL anhydrous toluene and 2.0 g γ-chloropropyl triethoxy silane (CPTES, with a molecular structure of $C_3H_6ClSi(OC_2H_5)_3$) were added thereto, after refluxed at 110° C. for 24 h, filtrated, washed with anhydrous ethanol for 3 times, and then oven-dried at 110° C. for 12 h, to obtain a macromolecular agent.

Then, the obtained macromolecular agent was added to a solution of 2.0 g 2-di-t-butylphosphine-2',4',6'-triisopropyl-biphenyl (CAS No.: 564483-19-8, as follows) in 100 mL benzonitrile, after reacting at 190° C. for 40 h, filtrated, washed respectively by ethanol and acetone for three times, and vacuum dried at 60° C. for 12 h, a supported quaternary phosphonium catalyst was obtained.

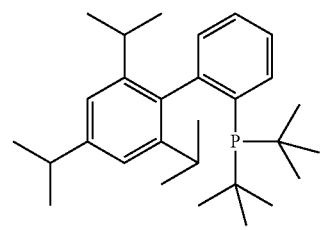 [SMILES: CC(C)c1cc(C(C)C)c(-c2ccccc2P(C(C)(C)C)C(C)(C)C)c(C(C)C)c1]

22.0 g ethylene carbonate, 32.0 g methanol and 1.1 g of the supported quaternary phosphonium catalyst were placed into a 100 ml autoclave (with the ratio by mol of methanol to ethylene carbonate of 4:1, and the ratio by weight of the supported quaternary phosphonium catalyst to ethylene carbonate of 0.05:1), and reacted at 100° C. for 4 h. Upon completion of the reaction, the autoclave was cooled down to the room temperature and evacuated. The liquid phase was sampled and subject to a gas chromatography analysis. The result is that, the ethylene carbonate conversion was 36.4%, the dimethyl carbonate selectivity was 97.4%, the ethylene glycol selectivity was 98.4%, and the elution loss D (%) determined was 0.4%.

Example 38

10.0 g carrier (Aerisol 200 produced by Degussa, with a specific surface area of 210 m$^2$/g) was placed into a 500 mL three-necked bottle, and then 200 mL anhydrous toluene and 2.0 g γ-chloropropyl triethoxy silane (CPTES, with a molecular structure of $C_3H_6ClSi(OC_2H_5)_3$ were added thereto, after refluxed at 110° C. for 24 h, filtrated, washed with anhydrous ethanol for 3 times, and then oven-dried at 110° C. for 12 h, to obtain a macromolecular agent.

Then, the obtained macromolecular agent was added to a solution of 2.0 g triallylphosphine (CAS No.: 16523-89-0, as follows) in 100 mL benzonitrile, after reacting at 190° C. for 40 h, filtrated, washed respectively by ethanol and acetone for three times, and vacuum dried at 60° C. for 12 h, a supported quaternary phosphonium catalyst was obtained.

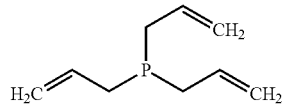

22.0 g ethylene carbonate, 32.0 g methanol and 1.1 g of the supported quaternary phosphonium catalyst were placed into a 100 ml autoclave (with the ratio by mol of methanol to ethylene carbonate of 4:1, and the ratio by weight of the supported quaternary phosphonium catalyst to ethylene carbonate of 0.05:1), and reacted at 100° C. for 4 h. Upon completion of the reaction, the autoclave was cooled down to the room temperature and evacuated. The liquid phase was sampled and subject to a gas chromatography analysis. The result is that, the ethylene carbonate conversion was 36.4%, the dimethyl carbonate selectivity was 97.4%, the ethylene glycol selectivity was 98.4%, and the elution loss D (%) determined was 0.4%.

We claim:

1. A process for producing a supported quaternary phosphonium catalyst, comprising a step of reacting a tertiary phosphine of the following formula (2) with a macromolecular agent of the following formula (3), wherein the ratio by weight of the tertiary phosphine to the macromolecular agent is 1 to 20 : 80 to 99,

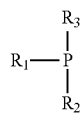 (2)

wherein $R_1$, $R_2$ and $R_3$ are different from or identical to each other, and are each independently selected from the group consisting of a $C_{6-20}$ aryl, or a $C_{6-20}$ aryl substituted by one or more $C_{1-6}$ straight-chain or branched alkyl or $C_{2-6}$ straight-chain or branched alkenyl, ------ represents a covalent bond,

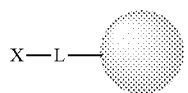 (3)

wherein X is a halogen atom, L is a bivalent bonding group,

is one or more carrier selected from the group consisting of silica, zeolite, and kieselguhr,
------ represents a covalent bond, and
wherein the reaction temperature is 100 to 190 ° C., and the reaction duration is 10 to 40 h.

2. The process according to claim 1, wherein the reaction temperature is 120 to 190 ° C., and the reaction duration is 10 to 30 h.

3. The process according to claim 1, wherein the macromolecular agent is produced by a reaction between the carrier and a halogenation agent of the following formula (4), wherein the ratio by weight of the halogenation agent to the carrier is 0.005 to 0.15: 1,

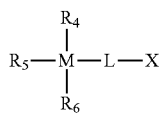 (4)

wherein X is a halogen atom, L is a bivalent bonding group, M is Ti, Si or Zr. $R_4$, $R_5$ and $R_5$ are different from or identical to each other, and each independently represents a $C_{1-4}$ straight-chain or branched alkoxy.

4. The process according to claim 3, wherein in the reaction between the carrier and the halogenation agent, the reaction temperature is 70 to 140° C., and the reaction duration is 1 to 60h.

5. The process according to claim 3, wherein said X is Cl, and the process further comprises a step of contacting the macromolecular agent with one or more modifying agent selected from the group consisting of a bromination agent and an iodization agent before reacting the macromolecular agent with the tertiary phosphine, wherein the ratio by weight of the modifying agent to the macromolecular agent is 0.01 to 1:1.

6. The process according to claim 1, wherein the ratio by weight of the tertiary phosphine to the macromolecular agent is 1 to 15:85 to 99, and in formula (3), L is a bivalent bonding group selected from the group consisting of an optionally substituted $C_{1-20}$ straight-chain or branched alkylene, an optionally substituted $C_{2-20}$ straight-chain or branched alkenylene, or an optionally substituted $C_{2-20}$ straight-chain or branched alkynylene, wherein the alkylene, the alkenylene or the alkynylene is optionally interfered by one or more interfering group selected from the group consisting of —O—, —S—, —$NR_a$—($R_a$ is a $C_{1-4}$ alkyl), and phenylene.

7. The process according to claim 6, wherein in formula (3), L is a $C_{2-8}$ straight-chain alkylene.

8. The process according to claim 3, wherein the ratio by weight of the halogenation agent to the carrier is 0.01 to 0.1:1, and in formula (4), L is a bivalent bonding group selected from the group consisting of an optionally substituted $C_{1-20}$ straight-chain or branched alkylene, an optionally substituted $C_{2-20}$ straight-chain or branched alkenylene, or an optionally substituted $C_{2-20}$ straight-chain or branched alkynylene, wherein the alkylene, the alkenylene or the alkynylene is optionally interfered by one or more interfering group selected from the group consisting of —O—, —S—, —$NR_a$—($R_a$ is a $C_{1-4}$ alkyl), and phenylene.

9. The process of claim 1, wherein the supported quaternary phosphonium catalyst comprises the following average molecular structure (I):

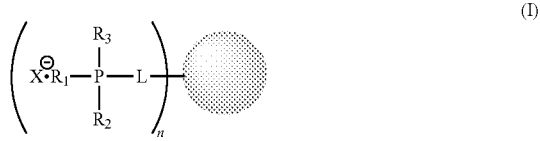
(I)

wherein X is a halogen atom, $R_1$, $R_2$ and $R_3$ are different from or identical to each other, and are each independently selected from the group consisting of a $C_{6-20}$ aryl, or a $C_{6-20}$ aryl substituted by one or more $C_{1-6}$ straight-chain or branched alkyl or $C_{2-6}$ straight-chain or branched alkenyl, L is a bivalent bonding group,

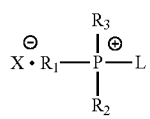

is one or more carrier selected from the group consisting of silica, zeolite, and kieselguhr,
------ represents a covalent bond,
• represents an ionic bond,
n is an averaged number such that the ratio by weight of the moiety

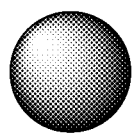

to the moiety

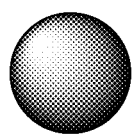

is 1 to 25:75 to 99.

10. The process of claim 9, wherein the supported quaternary phosphonium catalyst has an elution loss D of less than 1%, wherein the elution loss D is determined according to a method comprising weighting 2g of the supported quaternary phosphonium catalyst with a P content of P1 (unit: wt %), (1) suspending the supported quaternary phosphonium catalyst in 40ml methanol, stirring (at a stirring speed of 100 rpm) the resultant at 100° C. for 4h, then immediately filtering the resultant so as to separate the supported quaternary phosphonium catalyst, (2) then, suspending the separated supported quaternary phosphonium catalyst in 40ml methanol, stirring (at a stirring speed of 100 rpm) the resultant at 100° C. for 4h, then immediately filtering the resultant so as to separate the supported quaternary phosphonium catalyst, repeating the process (2) for further 10 times, and then determining the P content of the finally separated supported quaternary phosphonium catalyst as P2 (unit: wt %), and then calculating the elution loss D as follows:

$$D=(P1-P2)/P1\times 100\%.$$

11. The process of claim 1, wherein the reaction temperature is 190° C.

12. The process according to claim 9, wherein in the average molecular structure (I), L is a bivalent bonding group selected from the group consisting of an optionally substituted $C_{1-20}$ straight-chain or branched alkylene, an optionally substituted $C_{2-20}$ straight-chain or branched alkenylene, or an optionally substituted $C_{2-20}$ straight-chain or branched alkynylene, wherein the alkylene, the alkenylene, or the alkynylene is optionally interfered by one or more interfering group selected from the group consisting of —O—, —S—, —$NR_a$—($R_a$ is a $C_{1-4}$ alkyl) and phenylene, and the ratio by weight of the moiety

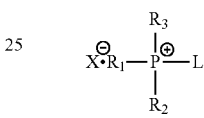

to the moiety

is 1 to 20:80 to 99.

13. The process according to claim 12, wherein in the average molecular structure (I), L is a $C_{2-8}$ straight-chain alkylene.

14. The process according to claim 10, wherein the supported quaternary phosphonium catalyst has an elution loss D of less than 0.5%.

15. A process for producing a dialkyl carbonate, comprising:
producing a supported quaternary phosphoniim catalyst by reacting a tertiary phosphine of the following formula (2) with a macromolecular agent of the following formula (3), wherein the ratio by weight of the tertiary phosphine to the macromolecular agent is 1 to 20:80 to 99.

(2)

wherein $R_1$, $R_2$ and $R_3$ are different from or identical to each other, and each independently slelcted from the group consisting of a $C_{6-20}$ aryl, or a $C_{6-20}$ aryl substituted by one or more $C_{1-6}$ straight-chain or branched alky or $C_{2-6}$ straight-chain or branched atkenyl, ─── represents a covalent bond,

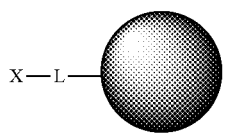 (3)

wherein X is a halogen atom, L is a bivalent bonding group,

is one or more carrier selected from the group consisting of silica, zeolite, and kieselguhr,
─── represents a covalent bond, and
wherein the reaction temperature is 100 to 190 °C., and the reaction duration is, 10 to 40 h; and
contacting a $C_{2-10}$ alkylene carbonate with a monohydric $C_{1-10}$ alkanol in the presence of the supported quaternary phosphonium catalyst.

16. The process according to claim 15, wherein in the step of contacting the $C_{2-10}$ alkylene carbonate with the monohydric $C_{1-10}$ alkanol in the presence of the supported quaternary phosphonium catalyst, the reaction temperature is 60 to 140 °C, the reaction duration is 0.1 to 20 h, the ratio by mol of the monohydric $C_{1-10}$ alkanol to the $C_{2-10}$ alkylene carbonate is 2 to 10:1, and the ratio by weight of the supported quaternary phosphonium catalyst to the $C_{2-10}$ alkylene carbonate is 0.005 to 0.5:1.

17. The process of claim 15, wherein the supported quaternary phosphonium catalyst comprises the following average molecular structure (I):

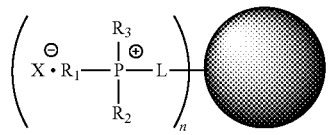 (I)

wherein X is a halogen atom, $R_1$, $R_2$ and $R_3$ are different from or identical to each other, and are each independently selected from the group consisting of a $C_{6-20}$ aryl, or a $C_{6-20}$ aryl substituted by one or more $C_{1-6}$ straight-chain or branched alkyl or $C_{2-6}$ straight-chain or branched alkenyl, L is a bivalent bonding group,

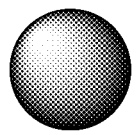

is one or more carrier selected from the group consisting of silica, zeolite, and kieselguhr,
─── represents a covalent bond,
• represents an ionic bond,
n is an averaged number such that the ratio by weight of the moiety

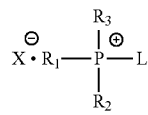

to the moiety

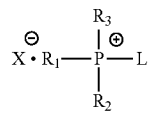

is 1 to 25:75 to 99.

18. The process according to claim 17, wherein in the average molecular structure (I), L is a bivalent bonding group selected from the group consisting of an optionally substituted $C_{1-20}$ straight-chain or branched alkylene, an optionally substituted $C_{2-20}$ straight-chain or branched alkenylene, or an optionally substituted $C_{2-20}$ straight-chain or branched alkynylene, wherein the alkylene, the alkenylene or the alkynylene is optionally interfered by one or more interfering group selected from the group consisting of —O—, —S—, —$NR_a$— ($R_a$ is a $C_{1-4}$ alkyl) and phenylene, and the ratio by weight of the moiety $$\overset{\ominus}{X} \cdot R_1 \!\!-\!\!\overset{R_3}{\underset{R_2}{\overset{|\oplus}{P}}}\!\!-\!\!L$$

to the moiety is 1 to 20:80 to 99.

19. The process according to claim 18, wherein in the average molecular structure (I), L is a $C_{2-8}$ straight-chain alkylene.

20. The process according to claim 17, wherein the supported quaternary phosphonium catalyst has an elution loss D of less than 1%, wherein the elution loss D is determined according to a method comprising weighting 2 g of the supported quaternary phosphonium catalyst with a P content of P1 (unit: wt %), (1) suspending the supported quaternary phosphonium catalyst in 40 ml methanol, stirring (at a stirring speed of 100 rpm) the resultant at 100° C. for 4 h, then immediately filtering the resultant so as to separate the supported quaternary phosphonium catalyst, (2) then, suspending the separated supported quaternary phosphonium catalyst in 40 ml methanol, stirring (at a stirring speed of 100 rpm) the resultant at 100° C. for 4 h then immediately filtering the resultant so as to separate the supported quaternary phosphonium catalyst, repeating the process (2) for further 10 times, and then determining the P content of the finally separated supported quaternary phosphonium catalyst as P2 (unit: wt %), and then calculating the elution loss D as follows:

$$D=(P1-P2)/P1 \times 100\%$$

21. The process according to claim 20, wherein the supported quaternary phosphonium catalyst has an elution loss 0 of less than 0.5%.

22. The process of claim 15, wherein in the reaction between the tertiary phosphine of formula (2) and the macromolecular agent of formula (3) the reaction temperature is 190° C.

* * * * *